United States Patent [19]

Gelotte et al.

[11] 4,111,946

[45] Sep. 5, 1978

[54] PREPARATION OF 3-(PYRIDINYL)-2-CYCLOHEXEN-1-ONES

[75] Inventors: Karl O. Gelotte, Nassau; Andrew W. Zalay, Albany; Malcolm R. Bell, East Greenbush, all of N.Y.

[73] Assignee: Sterling Drug Inc., New York, N.Y.

[21] Appl. No.: 820,402

[22] Filed: Jul. 29, 1977

Related U.S. Application Data

[62] Division of Ser. No. 737,392, Nov. 1, 1976, Pat. No. 4,075,217, which is a division of Ser. No. 668,451, Mar. 19, 1976, Pat. No. 4,026,900.

[51] Int. Cl.$^2$ .......................................... C07D 213/46
[52] U.S. Cl. ................................................. 260/297 R
[58] Field of Search .................................... 260/297 R

[56] References Cited

U.S. PATENT DOCUMENTS 4,026,900   5/1977   Gelotte et al. .................. 260/296 M

OTHER PUBLICATIONS

Marvel et al., J. Org. Chem., vol. 22, pp. 1451 to 1457 (1957).
Mohrle et al., Arch. Pharmaz., vol. 307, pp. 550 to 560 (1974).
Compagnon et al., Bull Soc Chim France 1968, pp. 4132 to 4136.
Ross et al., J. Org. Chem., vol. 29, pp. 2341 to 2350 (1964).
Beyer et al., Chem. Ber, vol. 90, pp. 592–598 (1957).
Houben–Weyl, Methoden der Organischen Chemie, Band IV (5th Ed.), part 2, p. 54 (1955).

*Primary Examiner*—John D. Randolph
*Attorney, Agent, or Firm*—Robert K. Bair; B. Woodrow Wyatt

[57] ABSTRACT

3-(4- or 3-Pyridinyl)-2-cyclohexen-1-ones (I) and their oxime derivatives are useful in preparing (3-aminophenyl)-pyridines, in turn, useful in preparing known antibacterial agents. Also shown is the preparation of I by starting with the reaction of methyl vinyl ketone with either 1-(pyridinyl)-1-(lower-tertiary-amino)-ethylene (II) or lower-alkyl 3-(pyridinyl)-3-oxopropanoate. Also shown is the process of converting I to its oxime, acylating the oxime and heating the acylated oxime under acidic conditions to produce N-(lower-acyl)-3-(pyridinyl)-aniline (VII), and hydrolyzing VII under aqueous alkaline conditions to produce the corresponding 3-(pyridinyl)aniline.

3 Claims, No Drawings

PREPARATION OF 3-(PYRIDINYL)-2-CYCLOHEXEN-1-ONES

CROSS-REFERENCE TO RELATED APPLICATIONS

This application is a division of copending application Ser. No. 737,392, filed Nov. 1, 1976 now U.S. Pat. No. 4,075,217, granted Feb. 21, 1978 in turn, a division of its copending application Ser. No. 668,451, filed Mar. 19, 1976 and now U.S. Pat. No. 4,026,900, issued May 31, 1977.

BACKGROUND OF THE INVENTION (a) Field of the Invention

This invention relates to 3-(4- or 3-pyridinyl)-2-cyclohexen-1-ones, to processes for their preparation and to a process for converting them to 3-(4- or 3-pyridinyl)anilines, which are useful as intermediates for preparing known antibacterial agents.

(b) Description of the Prior Art

The term "pyridyl" used in the following presentation of the prior art has the same meaning as "pyridinyl", the preferred term now used in Chemical Abstracts and used hereinbelow in describing the instant invention.

H. Beyer et al. [Chem. Ber. 90, 592–8 (1957)] show the reaction of 2-pyridylacetone with methyl vinyl ketone to produce 3-methyl-6-(2-pyridyl)-2-cyclohexen-1-one and its conversion by heating with sulfur to produce 3-methyl-6-(2-pyridyl)phenol.

C. S. Marvel et al. [J. Org. Chem. 22, 1451–1457 (1957)] report the following side reaction:

"The synthesis (of ethyl pyridalacetoacetates) was first attempted with pyridine-3-aldehyde by the method of Knoevenagel [Ber., 29, 172 (1896)], but it became apparent that even at the low temperature (−20°) or during subsequent steps a large amount of Michael addition of acetoacetic ester to ethyl 2-(3′-pyridal)acetoacetate (VII) was taking place, since distillation after the decarboxylation step yielded a 3-methyl-5-(3′-pyridyl)-Δ²-cyclohexenone (I). (The position of the double bond had not been definitely fixed in the cyclohexenone ring.

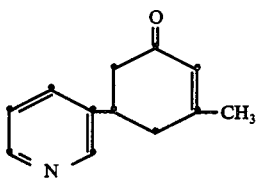

I

It may have migrated to the Δ⁵ position.) In order to avoid this side reaction, the condensation was run in an ether solution. In this manner the product crystallized as it was formed, and the ethyl 2-pyridalacetoacetates were obtained relatively free from acetoacetic ester."

N. C. Ross et al. [J. Org. Chem. 29, 2341–2350 (1964)] show the steps of reacting acetophenone with methyl vinyl ketone in the presence of lithium amide in anhydrous liquid ammonia to produce 1-phenylhexan-1,5-dione together with a cyclized product, 3-phenyl-3-hydroxycyclohexanone, which by dehydration is converted into 3-phenyl-2-cyclohexen-1-one. Ross et al. also report the following reaction "In the acetoethylation of 2-phenacylpyridine (XXIII) two compounds, XXIV and XXV, were obtained. In this connection, it should be pointed out that earlier 2-phenacylpyridine hydrochloride had been treated with methyl vinyl ketone and alcoholic potassium hydroxide by Beyer et al.

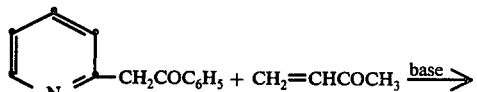

XXIII

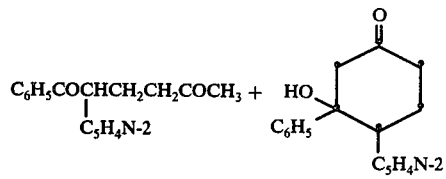

XXIV (m.p. 58.8–59.8)

XXV (m.p. 167.4–168.2)

[H. Beyer, W. Lassig, and G. Schudy, Ber., 90, 592 (1957)], who obtained a compound, m.p. 166°. Although they did not elucidate its structure, these workers claim that they obtained XXIV. From our work there is little doubt that they prepared XXV."

P. L. Compagnon et al. [Bull. Soc. Chim. Fr. 10, 4132–6 (1968] show the hydration of 7-(2-pyridyl)-1,2-heptyn-6-one in the presence of mecuric salts to produce a transitory 7-(2-pyridyl)heptan-2,6-dione which is said to automatically lose a molecule of water to produce 2-(2-pyridyl)-3-methyl-2-cyclohexen-1-one which is then catalytically hydrogenated in the presence of Raney nickel to produce 2-(2-pyridyl)-3-methylcyclohexan-1-one.

H. Mohrle et al. [Arch. Pharmazie 307, 550–560 (1974)] show the reaction of pyridine-3-aldehyde with two moles of ethyl acetoacetate and conversion of the resulting condensation product at −10° C. in the presence of diethylamine to produce 3-methyl-5-(3-pyridyl)-2-cyclohexen-1-one. Also, they established by use of NMR spectrum of said 2-cyclohexen-1-one that its double bond is at the 2-3 position instead of the 5-6 position, which had been presented by Marvel et al., supra, as a possibility.

F. M. Beringer et al. [J. Am. Chem. Soc. 75, 2635–2639 (1953)] show the preparation of 3-methyl-5-phenyl-2-cyclohexen-1-one from ethyl α,α-diacetyl-β-phenylglutarate, reaction of the 3-methyl-5-phenyl-2-cyclohexen-1-one with hydroxylamine hydrochloride to produce its oxime and then heating the oxime successively with acetic anhydride and then acetyl chloride to produce 3-methyl-5-phenylacetanilide and hydrolysis of said acetanilide with aqueous hydrochloric acid to produce 3-methyl-5-phenylaniline.

SUMMARY OF THE INVENTION

In a composition aspect, the invention relates to 3-PY-2-cyclohexen-1-ones (I) where PY is 4- or 3-pyridinyl or 4- or 3-pyridinyl having one or two lower-alkyl substituents, or its oxime derivative. These compounds are useful as intermediates in the preparation of 3-PY-anilines which, in turn, are useful as intermediates in the preparation of known antibacterial agents.

In a process aspect the invention resides in the process of reacting methyl vinyl ketone or precursor thereof with 1-PY-1-(lower-tertiary-amino)-ethylene (II), where PY is defined as above, and hydrolyzing in situ the resulting 1-(pyridinyl)-3-(lower-tertiary-amino)-1,3-cyclohexadiene (III), an enamine, preferably by heating III with a lower-alkanoic acid, an alkali lower-alkanoate and water, to produce said 3-PY-2-cyclohexen-1-ones (I). This process aspect is disclosed and claimed in copending divisional Application Ser. No. 870,753 pending, filed Jan. 19, 1978.

In another process aspect the invention resides in the process of reacting methyl vinyl ketone or precursor thereof with lower-alkyl 3-PY-3-oxopropanoate (IV), where PY is defined as above, in the presence of a basic condensing agent to produce lower-alkyl 5-oxo-2-(PY-carbonyl)hexanoate (V) and heating V under aqueous acidic conditions thereby hydrolyzing and decarboxylating V to produce 1-PY-hexan-1,5-dione (VI) and then reacting VI with a basic condensing agent to produce 3-PY-2-cyclohexen-1-one. Optionally, V can first be ring-closed by reacting it with a basic condensing agent to produce lower-alkyl 3-(pyridinyl)-2-cyclohexen-1-one-4-carboxylate which can be heated under aqueous acidic conditions to hydrolyze and decarboxylate said 4-carboxylate to produce 3-PY-2-cyclohexen-1-one.

In another process aspect the invention resides in the process of converting the 3-PY-2-cyclohexen-1-one (I) to its oxime, acylating the oxime and heating the acylated oxime under acidic conditions to produce N-(lower-acyl)-3-PY-aniline (VII) and hydrolyzing VII under aqueous alkaline or acid conditions to produce the corresponding 3-PY-aniline. In a preferred embodiment, the acylation and heating steps are combined by heating the oxime with a lower-alkanoic acid, a lower-alkanoic anhydride and hydrogen halide, to produce N-(lower-alkanoyl)-3-PY-aniline (VII) which is then hydrolyzed as above to produce 3-PY-aniline.

DETAILED DESCRIPTION INCLUSIVE OF PREFERRED EMBODIMENTS

In a composition aspect the invention resides in the 3-(pyridinyl)-2-cyclohexen-1-ones having Formula I

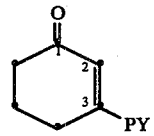

where PY is 4- or 3-pyridinyl or 4- or 3-pyridinyl having one or two lower-alkyl substituents, or its oxime derivative. The compounds of Formula I are useful as intermediates in the preparation of (3-aminophenyl)-pyridines which, as shown in U.S. Pat. No. 3,753,993, issued Aug. 21, 1973, are useful as intermediates in the preparation of 1,4-dihydro-1-(lower-alkyl)-4-oxo-7-(pyridinyl)-3-quinolinecarboxylic acids and lower-alkyl esters thereof which have antibacterial activity. Preferred embodiments are those of Formula I where PY is 4-pyridinyl, 3-pyridinyl, 2-methyl-4-pyridinyl and 2-methyl-5-pyridinyl (same as 6-methyl-3-pyridinyl). Particularly preferred embodiments are 3-(4-pyridinyl)-2-cyclohexen-1-one and its oxime.

In a process aspect the invention resides in the process of reacting methyl vinyl ketone or precursor thereof with 1-(pyridinyl)-1-(lower-tertiary-amino)-ethylene of the Formula II

where PY is defined as in Formula I above and NB is lower-tertiary-amino selected from piperidino, morpholino, pyrrolidino and di-(lower-alkyl)amino, and hydrolyzing in situ the resulting 1-(pyridinyl)-3-(lower-tertiary-amino)-1,3-cyclohexadiene of the Formula III

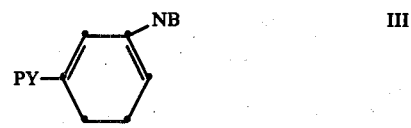

preferably by heating III with a lower-alkanoic acid, preferably acetic acid, an alkali lower-alkanoate, preferably potassium or sodium acetate, and water to produce the 3-(pyridinyl)-2-cyclohexen-1-one of Formula I.

In another process aspect the invention resides in the process of reacting methyl vinyl ketone or precursor thereof with lower-alkyl 3-(pyridinyl)-3-oxopropanoate of Formula IV

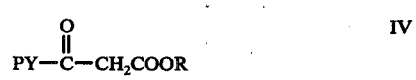

where PY is as defined as above for Formula I and R is lower-alkyl, in the presence of a basic condensing agent to produce lower-alkyl 5-oxo-2-(pyridinylcarbonyl)-hexanoate of Formula V

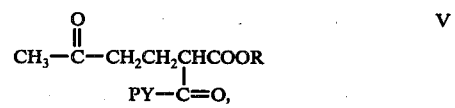

heating V under aqueous acidic conditions thereby hydrolyzing and decarboxylating V to produce 1-(pyridinyl)-1,5-dioxohexane of the Formula VI

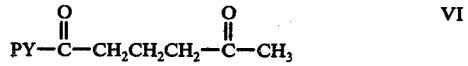

and then reacting VI with a basic condensing agent to produce 3-(pyridinyl)-2-cyclohexen-1-one of Formula I. Optionally, V can first be ring-closed by reacting it with a basic condensing agent to produce lower-alkyl 3-(pyridinyl)-2-cyclohexen-1-one-4-carboxylate which then can be heated under aqueous acidic conditions to hydrolyze and decarboxylate said 4-carboxylate to produce 3-(pyridinyl)-2-cyclohexen-1-one of Formula I.

In another process aspect the invention resides in the process of converting the 3-(pyridinyl)-2-cyclohexen-1-one of Formula I to its oxime, acylating the oxime, heating the resulting O-acyl oxime under acidic conditions to produce an N-(lower-acyl)-3-(pyridinyl)aniline of Formula VII

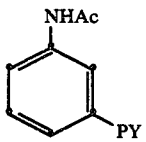

VII where PY is defined as in Formula I and Ac is a lower-acyl group, preferably acetyl, and hydrolyzing VII under aqueous alkaline or acid conditions to produce the corresponding 3-(pyridinyl)aniline. Optionally and preferably, the oxime is heated with a lower-alkanoic acid, a lower-alkanoic anhydride and a hydrogen halide, whereby the lower-alkanoate ester of the oxime is formed and is reacted in situ with the hydrogen halide, preferably gaseous hydrogen chloride, to produce VII where Ac is lower-alkanoyl. Optionally, Ac can be other low molecular acyl groups, e.g., benzoyl, tosyl, carbamoyl, 2,4-dimethoxybenzoyl, and the like.

The term "lower-alkyl", as used herein, e.g., as a substituent of the 4- or 3-pyridinyl group of formula I, means alkyl radicals having 1 to 6 carbon atoms, illustrated by methyl, ethyl, n-propyl, isopropyl, n-butyl, sec-butyl, tert-butyl, isobutyl, n-amyl, n-hexyl, and the like.

The term "lower-alkanoyl", as used herein, e.g., as one of the meanings for Ac in formula VII hereinabove, means alkanoyl radicals having from 2 to 6 carbon atoms, including the straight- and branch-chained radicals, illustrated by acetyl, propanoyl (n-propanoyl) butyryl (n-butanoyl), isobutyryl, (2-methyl-n-propanoyl) and caproyl (n-hexanoyl). Similarly, the term "lower" in "lower-alkanoic acid " and "lower-alkanoic anhydride" as used hereinabove is used to designate said acids and anhydrides as having from 2 to 6 carbon atoms and thereby providing said "lower-alkanoyl" radicals.

The 3-(pyridinyl-2-cyclohexen-1-ones having formula I are useful in free-base form or in the form of their acid-addition salts, and both forms are within the purview of the invention, and are considered to be one and the same invention. The acid-addition salts are simply a more convenient form for use; and, in practice, use of the salt form inherently amounts to use of the base form. In practicing our invention, we find it convenient to employ the methanesulfonate salt. However, other appropriately acceptable salts within the scope of the invention are those derived from mineral acids, such as hydrochloric acid, hydrobromic acid, hydriodic acid, nitric acid, phosphoric acid, sulfamic acid and sulfuric acid; and organic acids, such as acetic acid, tartaric acid, ethanesulfonic acid, benzenesulfonic acid, and the like, giving the hydrochloride, hydrobromide, hydriodide, nitrate, phosphate, sulfamate, sulfate, acetate, tartrate, ethanesulfonate and benzenesulfonate, respectively.

The acid-addition salts are prepared preferably by reacting the free base and acid in an organic solvent, e.g., ethanol, acetone, etc., in which the salt separates directly or can be obtained by concentration of the solution.

The molecular structures of said composition aspects of the invention were assigned on the basis of evidence provided by infrared, ultraviolet and nuclear magnetic resonance and mass spectra, by chromatographic mobilities, and by the correspondence of calculated and found values for the elementary analysis for representative examples.

The manner of making and using the instant invention will now be generally described so as to enable a person skilled in the art of organic chemistry to make and use the same, as follows:

In the preparation of the 3-(pyridinyl)-2-cyclohexen-1-ones (I), the step of reacting methyl vinyl ketone or precursor thereof with 1-(pyridinyl)-1-(lower-tertiary-amino)-ethylene (II) to produce 1-(pyridinyl)-3-(lower-tertiary-amino)-1,3-cyclohexadiene (III) is carried out by heating the reactants in the range of about 50° to 150° C., preferably between 80°-120° C., in a solvent inert under the reaction conditions, preferably a solvent immiscible with water, e.g., benzene or toluene. The next step is carried out by hydrolyzing in situ the resulting enamine (III) to product I. This hydrolysis can be run within a pH range of about 5 to 9, preferably at a pH of 6 to 8, and is conducted between about 75°-125° C., preferably 90°-110° C. This hydrolysis of the enamine III is conveniently and preferably carried out by heating III in situ with a lower-alkanoic acid, an alkali lower-alkanoate and water, preferably using acetic acid and potassium or sodium acetate.

Any precursor of methyl vinyl ketone, as used above and below, can be used in place of this highly active reagent. Thus, any compound or mixture of compounds readily converted to methyl vinyl ketone in situ can be used in the reactions described herein. For example, 4-diethylamino-2-butanone or a mixture of methyl iodide and 4-diethylamino-2-butanone on heating readily produces methyl vinyl ketone and could be used in place of methyl vinyl ketone.

The above-noted intermediate 1-(pyridinyl)-1-(lower-tertiary-amino)-ethylenes) (II) are generally known and are prepared by known methods. For example, a 4- or 3-acetyl pyridine is refluxed with a secondary amine of the formula H—NB, e.g., piperidine, morpholine, pyrrolidine, diethylamine, diisopropylamine, and the like, in the presence of tosyl acid, preferably under an inert atmosphere, e.g., nitrogen. The reaction is conveniently carried out with a continuous water separator connected to the reaction vessel and the reaction is run until no more water is collected. This particular procedure conveniently provides a solution of the 1-PY—1—(NB)=CH$_2$ (II) in a toluene or benzene solution which can be used directly in the reaction with methyl vinyl ketone to produce III. Kost et al. [Doklady Akad. Nauk S.S.S.R. 130, 326-8 (1960); C.A. 54, 11,015c (1960)] prepared 2-methyl-5-(1-piperidinoethenyl)pyridine [same as 1-(2-methyl-5-pyridyl)-1-piperidinoethylene] by refluxing 2-methyl-5-(1-bromoethenyl)pyridine with piperidine. Naef et al. [Helvetica Chimica Acta 45, 1018–1026 (1962)] show the conversion of 3-acetylpyridine by reaction with phosphorous pentachloride to produce 3-(1-chlorovinyl)pyridine and 3-(1,1-dichloroethyl)pyridine, and the heating at 175° C. of 3-(1-chlorovinyl)-pyridine with more than a two molar excess of piperidine to produce 1-(3-pyridinyl)-1,2-dipiperidinoethane.

The preparation of lower-alkyl 5-oxo-2-(pyridinylcarbonyl)hexanoate (V) by reacting methyl vinyl ketone or precursor with lower-alkyl 3-(pyridinyl)-3-oxopropanoate (IV) is carried out preferably by mixing the reactants in a suitable solvent in the presence of a basic condensing agent. The reaction is conveniently run using, as a solvent, a combination of benzene and a lower-alkanol, preferably methanol or ethanol, and an alkali lower-alkoxide, preferably sodium methoxide or sodium ethoxide, respectively, as the basic condensing agent. In practicing the invention, the reaction was carried out using benzene, methanol and sodium methoxide. Other basic condensing agents and solvents include: an alkali hydroxide or tetra-(lower-alkyl)- or tri-(lower-alkyl)-benzyl-ammonium hydroxide in a lower-alkanol, preferably NaOH, KOH, tetramethylammonium hydroxide or benzyltrimethylammonium hydroxide in methanol or ethanol; sodium hydride, lithium diethylamide, lithium diisopropylamide, and the like, in an aprotic solvent, e.g., tetrahydrofuran, acetonitrile, ether, benzene, dioxan, and the like. The reaction is conveniently run at room temperature and can be run at higher temperatures, e.g., up to about 120° C., but to no particular advantage. The resulting lower-alkyl 5-oxo-2-(pyridinylcarbonyl)hexanoate is stored in a refrigerator under nitrogen until used in the next step.

The conversion of lower-alkyl 5-oxo-2-(pyridinylcarbonyl)hexanoate (V) to 1-(pyridinyl)-1,5-dioxohexane (VI) is conveniently carried out by heating said hexanoate (V) under aqueous acidic conditions, preferably aqueous sulfuric acid, whereupon hydrolysis and decarboxylation take place. This reaction is conveniently carried out at a temperature between 80° and 120° C. These same reaction conditions can be used to convert lower-alkyl 3-(pyridinyl)-2-cyclohexen-1-one-4-carboxylate to 3-(pyridinyl)-2-cyclohexen-1-one.

The reaction of the 1-(pyridinyl)hexan-1,5-dione (VI) with a basic condensing agent to produce 3-(pyridinyl)-2-cyclohexen-1-one (I) is preferably carried out using aqueous alkali hydroxide solution at about 25° to 30° C. Also, there can be used other basic condensing agents and solvents such as those given hereinabove in the reaction between methyl vinyl ketone and lower-alkyl 3-(pyridinyl)-3-oxopropanoate (IV). These same reaction conditions can be used to convert lower-alkyl 5-oxo-2-(pyridinylcarbonyl)hexanoate to lower-alkyl 3-(pyridinyl)-2-cyclohexen-1-one-4-carboxylate.

The conversion of 3-(pyridinyl)-2-cyclohexene-1-one (I) to its oxime is carried out by reacting I with hydroxylamine, preferably as its hydrochloride, in the presence of an acid-acceptor, preferably using a suitable solvent. In practicing the invention, we found it convenient to run the reaction using pyridine as both the acid-acceptor and solvent. Also convenient are sodium acetate as the acid-acceptor and aqueous ethanol as the solvent. Other known acid-acceptors and solvents can be used, as well as other acid-addition salts of hydroxylamine.

The conversion of the oxime of 3-(pyridinyl)-2-cyclohexen-1-one to the corresponding N-(lower-acyl)-3-(pyridinyl)aniline (VII) is carried out by acylating said oxime with any appropriate acylating agent, e.g., anhydride, acid halide, etc., using conventional acylating means and then heating the resulting O-(lower-acyl) oxime derivative under acidic conditions, preferably in the presence of a strong mineral acid. The acylation and subsequent heating step are preferably run in combination by heating the oxime with a lower-alkanoic acid, a lower-alkanoic anhydride and hydrogen halide, preferably acetic acid, acetic anhydride and hydrogen chloride gas, respectively. The reaction is conveniently run in the range of about 80° to 140° C, preferably 100° to 120° C.

The hydrolysis of N-(lower-acyl)-3-(pyridinyl)-aniline (VII) is carried out by heating VII under aqueous alkaline or acid conditions until hydrolysis is complete. The hydrolysis is conveniently carried out in refluxing 35% aqueous sodium hydroxide solution or in an aqueous mineral acid, for example, aqueous hydrochloric acid. Whether alkaline or acidic hydrolysis, the reaction is conveniently run by refluxing the aqueous alkaline or acidic reaction mixture, the reaction temperature being in the range of about 80° to 150° C., preferably about 90°–110° C.

The following examples will further illustrate the invention without, however, limiting it thereto.

A. 3-(3- OR 4-PYRIDINYL)-2-CYCLOHEXEN-1-ONES FROM 3- OR 4-ACETYLPYRIDINES VIA 1-(3- OR 4-PYRIDINYL)-1-(TERTIARY-AMINO)ETHYLENES

A-1. 3-(4-Pyridinyl)-2-cyclohexen-1-one — In a 5-liter 3-necked flask fitted with a stirrer, a gas inlet tube, a continuous water separator and a reflux condenser, and, under a continuous stream of nitrogen, a mixture containing 465 g. of morpholine, 2500 ml. of toluene and 4 g. of tosyl acid (p-toluenesulfonic acid) was refluxed for about one hour to remove trace amounts of water. To the stirred reaction mixture was added 410 g. of freshly distilled 4-acetylpyridine in a steady stream and refluxing was continued until no more water was collected (about 48 hours). The reaction mixture was cooled to 4° C., stirred 2 minutes with 400 ml. of ice cold saturated sodium bicarbonate solution; the aqueous layer was removed; and, the organic layer was washed three times with ice cold water, dried over anhydrous potassium carbonate and filtered to yield a solution containing 1-(4-pyridinyl)-1-(morpholino)ethylene. To this toluene solution of 1-(4-pyridinyl)-1-(morpholino)ethylene at room temperature was added with stirring 238 g. of freshly distilled methyl vinyl ketone. The resulting reaction mixture was stirred at room temperature for 30 minutes and then heated at reflux overnight (about 16 hours) under nitrogen. The resulting clear rose-wine colored solution containing 1-(4-pyridinyl)-3-morpholino-1,3-cyclohexadiene was cooled slightly and to it was added a solution containing 200 g. of potassium acetate, 400 ml. of acetic acid and 400 ml. of water. The resulting mixture was then brought to reflux and kept refluxing for 4 hours. The solvent was distilled off under reduced pressure and the partly solid residue was dissolved in water. The aqueous solution was basified with 35% aqueous sodium hydroxide solution. The alkaline mixture was extracted three times with methylene dichloride; and the combined extracts were washed four times with water; and the organic layer was dried over anhydrous potassium carbonate, filtered and concentrated to dryness. The residual oil was distilled under high vacuum to distill off about 35 g. of material at 45°–55° C. and 0.025–0.005 mm., said material being mostly recovered 4-acetylpyridine. The residual oil was cooled in an ice bath and solidified readily when triturated with a glass rod. There was added 100 ml. of dry ether and the resulting mixture was kept in an ice bath for two hours. The solid was then collected, washed with two 100 ml. portions of ice cold ether and dried in vacuo at 40° C. to yield 278 g. of 3-(4-pryridinyl)-2-cyclohexen-1-one, m.p. 66°–69° C. The mother liquor was concentrated in vacuo to remove the solvent; the residue was dissolved in isopropyl alcohol and the solution treated with about 110 g. of methanesulfonic acid with cooling to slight acidity. The mixture was cooled well; the heavy precipitate was collected, washed with dry acetone and dried in a vacuum oven at 40° C. to yield 94 g. of 3-(4-pyridinyl)-2-cyclohexen-1-one methanesulfonate, m.p.

168°–175° C. The methanesulfonate salt was dissolved in water and to the solution was added ammonium hydroxide to basicity; the basic mixture was extracted three times with methylene dichloride; and the combined extracts were concentrated in vacuo to remove the methylene dichloride. The residue solified after which it was treated with a small amount of dry ether, collected by filtration and dried to yield 49 g. of 3-(4-pyridinyl)-2-cyclohexen-1-one, m.p. 69°–67° C., the total yield of the product thus being 327 g. or 57%.

A-2. 3-(3-Pyridinyl)-2-cyclohexen-1-one — A mixture containing 121.1 g. of 3-acetylpyridine, 90.0 g. of morpholine, 500 ml. of toluene and 0.5 g. of p-toluenesulfonic acid was refluxed with a continuous water separator attached to the reaction vessel. Refluxing was continued for 22 hours after which time the theoretical quantity of water (18 ml.) had been collected. The reaction mixture was concentrated in vacuo and the remaining oil was taken up in 250 ml. of dry benzene. To the benzene solution containing 1-(3-pyridinyl)-1-(morpholino)ethylene was added 70.1 g. of methyl vinyl ketone and the resulting mixture was refluxed for six hours and then allowed to stand overnight at room temperature. The mixture was concentrated in vacuo and to the remaining oil containing 1-(3-pyridinyl)-3-morpholino-1,3-cyclohexadiene was added 160 ml. of water, 160 ml. of acetic acid, 80 g. of sodium acetate trihydrate, and the resulting mixture was refluxed for 3 and one-half hours and then concentrated in vacuo. The remaining material was diluted with an equal volume of water; the aqueous solution was made alkaline with 35% aqueous sodium hydroxide solution; the alkaline solution was extracted three times with methylene dichloride; the extract was washed with water, dried over anhydrous magnesium sulfate and concentrated in vacuo to remove the solvent; and, the remaining oil was distilled under reduced pressure, collecting the fraction boiling at 125°–170° C. at 0.15 mm. This material was redistilled under reduced pressure, collecting the fraction boiling at 135°–141° C. at 0.15 mm. The resulting fraction crystallized to yield 57.5 g. of 3-(3-pyridinyl)-2-cyclohexen-1-one, m.p. 70°–73° C.

A-3. 3-(2-Methyl-5-pyridinyl)-2-cyclohexen-1-one — A mixture containing 84.1 g. of 5-acetyl-2-methylpyridine, 61 g. of morpholine, 500 ml. of toluene and 1.0 g. of p-toluenesulfonic acid was refluxed with stirring overnight (about 15 hours) with a continuous water separator connected to the reaction vessel. A total of 13 ml. of water was collected. The reaction mixture was concentrated in vacuo and the oily residue was taken up in 250 ml. of dry benzene. To the benzene solution containing 1-(2-methyl-5-pyridinyl)-1-(morpholino)ethylene was then added 43.6 g. of methyl vinyl ketone and the layer was refluxed for 24 hours. The reaction mixture was concentrated in vacuo and to the residual material containing 1-(2-methyl-5-pyridinyl)-3-morpholino-1,3-cyclohexadiene was added 60 g. of sodium acetate trihydrate, 120 ml. of water and 120 ml. of acetic acid. The resulting mixture was concentrated in vacuo. To the semi-solid residual material was added 200 ml. of water and the resulting mixture basified with 35% aqueous sodium hydroxide solution. The two layers were separated and the heavier aqueous layer was extracted three times with chloroform. The chloroform extract was combined with the upper organic layer. The resulting solution was dried over anhydrous magnesium sulfate and concentrated in vacuo. The remaining oil was distilled under reduced pressure, collecting a fraction boiling at 110°–205° C. at 0.11 mm. The oily material was redistilled under reduced pressure to yield a fraction of 13.1 g. of 3-(2-methyl-5-pyridinyl)-2-cyclohexen-1-one, b.p. 120°–150° C. at 0.11 mm. About 39 g. of the starting 5-acetyl-2-methylpyridine was recovered.

Following the procedure described in Example A-2 but using in place of 3-acetylpyridine a molar equivalent quantity of the appropriate 3- or 4-actylpyridine, the 3-(3- or 4-pyridinyl)-2-cyclohexen-1-ones of Examples A-4 thru A-9 are obtained.

A-4. 3-(2-Methyl-4-pyridinyl)-2-cyclohexen-1-one using 4-acetyl-2-methylpyridine.

A-5. 3-(5-Ethyl-3-pyridinyl)-2-cyclohexen-1-one using 3-acetyl-5-ethylpyridine.

A-6. 3-(4-Methyl-3-pyridinyl)-2-cyclohexen-1-one using 3-acetyl-4-methylpyridine.

A-7. 3-(2,4-Dimethyl-3-pyridinyl)-2-cyclohexen-1-one using 3-acetyl-2,4-dimethylpyridine.

A-8. 3-(2,6-Dimethyl-3-pyridinyl)-2-cyclohexen-1-one using 3-acetyl-2,6-dimethylpyridine.

A-9. 3-(2,6-Dimethyl-4-pyridinyl)-2-cyclohexen-1-one using 4-acetyl-2,6-dimethylpyridine.

Following the procedure described in Example A-2 but using in place of morpholine a molar equivalent quantity of piperidine, pyrrolidine or diethylamine, there is obtained the same final product, 3-(3-pyridinyl)-2-cyclohexen-1-one; however, the following respective intermediates are first produced: 1-(3-pyridinyl)-1-(piperidino)ethylene, 1-(3-pyridinyl)-1-(pyrrolidino)ethylene or 1-(3-pyridinyl)-1-(diethylamino)ethylene and 1-(3-pyridinyl)-3-(piperidino)-1,3-cyclohexadiene, 1-(3-pyridinyl)-3-(pyrrolidino)-1,3-cyclohexadiene or 1-(3-pyridinyl)-3-(diethylamino)-1,3-cyclohexadiene.

B. 3-(3- OR 4-PYRIDINYL)-2-CYCLOHEXEN-1-ONES FROM ALKYL 3-(3- OR 4-PYRIDINYL)-3-OXOPROPANOATES VIA 1-(3- OR 4-PYRIDINYL)-HEXAN-1,5-DIONES

B-1. 3-(4-Pyridinyl)-2-cyclohexen-1-one — To a stirred solution containing 77 g. of ethyl isonicotinoylacetate in a mixture of 600 ml. of benzene and 200 ml. of methanol, said solution kept under nitrogen, was added 0.2 g. of sodium methoxide and the resulting mixture was stirred for a few minutes. To the stirred reaction mixture was then added dropwise over a period of 35 to 40 minutes without external cooling a solution containing 30.8 g. of methyl vinyl ketone in 120 ml. of benzene and 40 ml. of methanol. At the end of the addition the temperature had risen to 30° C. The reaction mixture was then stirred for 5 hours, keeping the temperature about 30° C. The reaction mixture was then washed with 300 ml. of saturated sodium chloride solution and the washings back extracted once with benzene. The organic layer plus back extract was dried over anhydrous magnesium sulfate, treated with decolorizing charcoal and filtered. The filtrate was concentrated in vacuo and then any traces of solvent were removed under high vacuum to yield 104.5 g. of ethyl 2-(isonicotinoyl)-5-oxohexanoate which was stored in a refrigerator under nitrogen until used in the next step. A 116 g. portion of ethyl 2-(isonicotinoyl)-5-oxohexanoate dissolved in a mixture containing 220 ml. of concentrated sulfuric acid in 660 ml. of water. The resulting reaction mixture was slowly heated with stirring. Evolution of carbon dioxide was observed at about 50° C.;

after about 90 minutes the temperature had reached 95° C. and carbon dioxide was still being evolved. The reaction mixture was kept at this temperature for an additional thirty minutes after which the evolution of carbon dioxide had practically ceased. The reaction mixture which contained 1-(4-pyridinyl)hexan-1,5-dione was kept at this temperature for an additional five minutes and then cooled to 25° C. and treated with 35% aqueous sodium hydroxide solution in a fine stream until basic, requiring about 600 ml. of the sodium hydroxide solution. The temperature was kept at about 25°–30° C. throughout the addition period and for one full hour thereafter. The reaction mixture was then extracted four times with chloroform. The extracts were combined, dried over anhydrous magnesium sulfate and treated with decolorizing charcoal, filtered and concentrated in vacuo to remove the solvent. The residue was dissolved in 750 ml. of isopropyl alcohol and to this solution with cooling was added one equivalent (43 g.) of methanesulfonic acid, whereupon the product quickly precipitated. The mixture was cooled to 5° C. and the product was collected, washed successively with fresh isopropyl alcohol and then ether, and dried in vacuo at 60° C. to yield 101 g. of 3-(4-pyridinyl)-2-cyclohexen-1-one methanesulfonate, m.p. 174°–177° C. The 101 g. of product was recrystallized from 500 ml. of absolute ethanol to yield 94 g. of recrystallized product, m.p. 178°–181° C. (80% yield).

The above intermediate ethyl isonicotinoylacetate is a known compound [Pinner, Chem. Ber. 34, 4249 (1901)] and can be prepared by various means, for example, from isonicotinic acid by the following procedure: To a stirred suspension containing 123 g. of isonicotinic acid in 750 ml. of toluene was added 131 g. of thionyl chloride followed by the addition of 1 ml. of dimethylformamide. The mixture was heated to 100° C. for 90 minutes, cooled to 90° C., and 80 ml. of absolute ethanol was added dropwise very carefully to the stirred reaction mixture. The temperature was then brought back up to 100° C. and kept there for ninety minutes and then chilled in an ice bath. The separated precipitate was collected, washed with ether and dried in a vacuum oven at 70° C. for two hours to yield 180 g. (96% yield) of ethyl isonicotinate hydrochloride, m.p. 166°–168° C. Since this ester hydrochloride tends to sublime in the vacuum oven, it is not necessary to dry the product at this stage and the base can be liberated from the wet product. The ethyl isonicotinate hydrochloride was dissolved in 1 liter of cold water, the solution covered with ether and the mixture cooled in an ice bath. Then 90 g. of sodium bicarbonate was added carefully to the stirred mixture. The layers were separated, and the aqueous phase was extracted twice with ether and the extract combined with the original ether layer. The combined ether solutions were dried over anhydrous magnesium sulfate and concentrated in vacuo to remove the ether, thereby yielding 136 g. of ethyl isonicotinate, $n_D^{25} = 1.490$, which distilled at 97°–98° C. and 10–11 mm. to yield 129 g. of said compound, $n_D^{25} = 1.4975$. To 4 liters of refluxing ethanol was added 115 g. of sodium so as to maintain steady reflux. The sodium ethoxide solution was concentrated under vacuum to a white powder. To this was added a solution of 498 g. of ethyl isonicotinate and 580 g. of ethyl acetate in one portion. Solution was complete in thirty minutes and the reaction mixture was refluxed for 20 hours. The reddish-orange solution was poured into 5 liters of water and washed twice with ether. The aqueous layer was then acidified with acetic acid and the oil that separated was collected. The aqueous layer was saturated with sodium chloride and the mixture was extracted with ethyl acetate. These extracts were combined with the oil, the solution was dried, treated with decolorizing charcoal and filtered; and, the filtrate was concentrated to give 582 g. of red oil which crystallized on cooling. This oil was dissolved in approximately 400 ml. of warm methanol and 1 liter of water was added. The mixture was cooled to below 0° C. and the separated product was collected, thereby yielding 490 g. of ethyl isonicotinoylacetate, m.p. 59°–61° C. Concentration of the mother liquor gave an additional 15 g., 58°–60° C., for a total yield of 505 g. (80% yield).

B-2. 3-(2-Methyl-5-pyridinyl)-2-cyclohexen-1-one — To a stirred solution containing 48 g. of ethyl 3-(2-methyl-5-pyridinyl)-3-oxopropanoate in a mixture of 300 ml. of dry benzene and 100 ml. of dry methanol, said solution kept under nitrogen, was added 0.1 g. of sodium methoxide followed by the dropwise addition over a period of about one hour of the solution containing 16 g. of freshly distilled methyl vinyl ketone in a mixture of 60 ml. of benzene and 10 ml. of methanol. After the reaction had proceeded slowly at room temperature overnight, an additional 0.1 g. of sodium methoxide plus 4 ml. of additional methyl vinyl ketone were added and the reaction mixture was heated with stirring at 40° C. for 8 hours. The solvent was distilled off in vacuo; 300 ml. of benzene was added; the benzene solution was washed once with brine, dried over anhydrous sodium sulfate and heated in vacuo to remove the benzene thereby yielding a quantative yield (63.5 g.) of ethyl 2-(2-methyl-5-pyridinylcarbonyl)-5-oxohexanoate which was added to a mixture containing 95 ml. of concentrated sulfuric acid and 185 ml. of water. The acidic reaction mixture was slowly heated. After about 30 minutes, the temperature reached 55° C. and the evolution of carbon dioxide became noticeable. The temperature of the reaction mixture was maintained at 65° C. for about one hour and then heated to 80° C. and held there for several minutes. By this time the evolution of carbon dioxide appeared to be over. The reaction mixture was cooled and poured into a solution of 305 g. of potassium carbonate in 1 liter of ice water. Chloroform was added; the mixture was shaken well and filtered to remove the precipitated potassium sulfate; and, the layers were separated. The aqueous layer was extracted further with chloroform; the combined chloroform extracts were dried over anhydrous sodium sulfate and filtered; the dried filtrate was heated in vacuo to remove the chloroform to yield, after air-drying, 27.4 g. (80%) of 1-(2-methyl-5-pyridinyl)hexan-1,5-dione, a tan solid melting at 85°–87° C.

A 72.2 g. portion of 1-(2-methyl-5-pyridinyl)hexan-1,5-dione was dissolved in 200 ml. of methanol and added to a solution containing 50 g. of sodium hydroxide in 500 ml. of water plus 100 ml. of methanol. The reaction mixture was stirred for one hour at room temperature and the methanol was then distilled off in vacuo at a low temperature. The remaining aqueous mixture was extracted four times with ether; the ether extracts were combined, dried over anhydrous sodium sulfate and filtered; and, the dried ether solution was stripped in vacuo to remove the ether and to yield 54 g. (82% yield) of 3-(2-methyl-5-pyridinyl)-2-cyclohexen-1-one. This 54 g. portion of 2-(2-methyl-5-pyridinyl)-2-cyclohexen-1-one was converted, as in Example C-3, to 36.0 g. (62% yield) of the corresponding oxime derivative, m.p. 171°–173° C. The 10 g. portion of this oxime was converted, as in Example D-3, to 6.4 g. of 5-(3-aminophenyl)-2-methylpyridine, m.p. 115°–116° C., using 8.5 ml. of acetic anhydride and 70 ml. of acetic acid and gaseous hydrogen chloride for one hour while heating the reaction mixture at 80°–90° C.

The above intermediate ethyl 3-(2-methyl-5-pyridinyl)-3-oxopropanoate was prepared from ethyl 2-methyl-5-pyridinecarboxylate, aslo known as ethyl 6-methylnicotinate, a known compound [Plattner et al. Helv. Chim. Acta 37, 1379 (1954)], as follows: To 500 ml. of well-stirred ethanol warmed on a steam bath under an atmosphere of nitrogen was added small pieces of 15.5 g. of sodium over a period of about ninety minutes. The ethanol was distilled-off in vacuo and the remaining white residue was heated at 90° C. for 2 hours under reduced pressure. To the white residue was added a solution containing 70 g. of ethyl 2-methyl-5-pyridinecarboxylate in 92 ml. of ethyl acetate. The resulting dark red solution was stirred at room temperature for 30 minutes and then refluxed overnight (about 15 hours). The reaction mixture was poured into 1 liter of cold water and the resulting mixture was extracted with two 200 ml. portions of ether. The aqueous layer was acidified with 42 ml. of acetic acid to a pH of about 7–8 and the mixture was extracted with three 200 ml. portions of ether. The combined ether extracts were dried over anhydrous magnesium sulfate and the ether removed in vacuo to yield 74 g. of red liquid. The aqueous layer was saturated with salt, the mixture extracted twice with ether, the ether extract dried over anhydrous sodium sulfate and ether distilled-off in vacuo to yield an additional 9 g. of red liquid. The combined 83 g. of red liquid was then distilled under reduced pressure to yield 45 g. of ethyl 3-(2-methyl-5-pyridinyl)-3-oxopropanoate, b.p. 108°–114° C. at 0.15–0.30 mm.

Following the procedure described in Example B-1 but using in place of isonicotinic acid a corresponding molar equivalent quantity of the appropriate pyridinecarboxylic acid, the corresponding 3-(pyridinyl)-2-cyclohexen-1-ones of Examples B-3 thru B-13 are obtained after successively producing the respective lower-alkyl 3-(pyridinyl)-3-oxopropanoate, lower-alkyl 2-(pyridinylcarbonyl)-5-oxohexanoate and 1-(pyridinyl)hexan-1,5-diones.

B-3. 3-(3-Pyridinyl)-2-cyclohexen-1-one starting with nicotinic acid and successively producing ethyl nicotinoylacetate, ethyl 2-(nicotinoyl)-5-oxohexanoate and 1-(3-pyridinyl)hexan-1,5-dione.

B-4. 3-(2-Methyl-4-pyridinyl)-2-cyclohexen-1-one starting with 2-methyl-4-pyridinecarboxylic acid (alternatively named 2-methylisonicotinic acid) and successively producing ethyl 3-(2-methyl-4-pyridinyl)-3-oxopropanoate, ethyl 2-(2-methyl-4-pyridinecarbonyl)-5-oxohexanoate and 1-(2-methyl-4-pyridinyl)hexan-1,5-dione.

B-5. 3-(3-Methyl-4-pyridinyl)-2-cyclohexen-1-one starting with 3-methyl-4-pyridinecarboxylic acid and successively producing ethyl 3-(3-methyl-4-pyridinyl)-3-oxopropanoate, ethyl 2-(3-methyl-4-pyridinecarbonyl)-5-oxohexanoate and 1-(3-methyl-4-pyridinyl)hexan-1,5-dione.

B-6. 3-(2-Ethyl-4-pyridinyl)-2-cyclohexen-1-one starting with 2-ethyl-4-pyridinecarboxylic acid and successively producing ethyl 3-(2-ethyl-4-pyridinyl)-3-oxopropanoate, ethyl 2-(2-ethyl-4-pyridinecarbonyl)-5-oxohexanoate and 1-(2-ethyl-4-pyridinyl)hexan-1,5-dione.

B-7. 3-(2-Methyl-3-pyridinyl)-2-cyclohexen-1-one starting with 2-methyl-3-pyridinecarboxylic acid and successively producing ethyl 3-(2-methyl-3-pyridinyl)-3-oxopropanoate, ethyl 2-(2-methyl-3-pyridinecarbonyl)-5-oxohexanoate and 1-(2-methyl-3-pyridinyl)-hexan-1,5-dione.

B-8. 3-(4-Methyl-3-pyridinyl)-2-cyclohexen-1-one starting with 4-methyl-3-pyridinecarboxylic acid and successively producing ethyl 3-(4-methyl-3-pyridinyl)-3-oxopropanoate, ethyl 2-(4-methyl-3-pyridinecarbonyl)-5-oxohexanoate and 1-(4-methyl-3-pyridinyl)-hexan-1,5-dione.

B-9. 3-(2,6-Dimethyl-4-pyridinyl)-2-cyclohexen-1-one starting with 2,6-dimethyl-4-pyridinecarboxylic acid and successively producing ethyl 3-(2,6-dimethyl-4-pyridinyl)-3-oxopropanoate, ethyl 2-(2,6-dimethyl-4-pyridinecarbonyl)-5-oxohexanoate and 1-(2,6-dimethyl-4-pyridinyl)hexan-1,5-dione.

B-10. 3-(5-Ethyl-2-methyl-4-pyridinyl)-2-cyclohexen-1-one starting with 5-ethyl-2-methyl-4-pyridinecarboxylic acid and successively producing ethyl 3-(5-ethyl-2-methyl-4-pyridinyl)-3-oxopropanoate, ethyl 2-(5-ethyl-2-methyl-4-pyridinecarbonyl)-5-oxohexanoate and 1-(5-ethyl-2-methyl-4-pyridinyl)hexan-1,5-dione.

B-11. 3-(2,6-Dimethyl-3-pyridinyl)-2-cyclohexen-1-one starting with 2,6-dimethyl-3-pyridinecarboxylic acid and successively producing ethyl 3-(2,6-dimethyl-3-pyridinyl)-3-oxopropanoate, ethyl 2-(2,6-dimethyl-3-pyridinecarbonyl)-5-oxohexanoate and 1-(2,6-dimethyl-3-pyridinyl)hexan-1,5-dione.

B-12. 3-(2-Ethyl-5-methyl-3-pyridinyl)-2-cyclohexen-1-one starting with 2-ethyl-5-methyl-3-pyridinecarboxylic acid and successively producing ethyl 3-(2-ethyl-5-methyl-3-pyridinyl)-3-oxopropanoate, ethyl 2-(2-ethyl-5-methyl-3-pyridinecarbonyl)-5-oxohexanoate and 1-(2-ethyl-5-methyl-3-pyridinyl)hexan-1,5-dione.

B-13. 3-(4-Ethyl-5-methyl-3-pyridinyl)-2-cyclohexen-1-one starting with 4-ethyl-5-methyl-3-pyridinecarboxylic acid and successively producing ethyl 3-(4-ethyl-5-methyl-3-pyridinyl)-3-oxopropanoate, ethyl 2-(4-ethyl-5-methyl-3-pyridinecarbonyl)-5-oxohexanoate and 1-(4-ethyl-5-methyl-3-pyridinyl)hexan-1,5-dione.

B-14. 3-(4-Pyridinyl)-2-cyclohexen-1-one is obtained by modifying the procedure described in Example B-1 as follows: Ethyl isonicotinoylacetate and methyl vinyl ketone are reacted as in Example B-1 to yield ethyl 2-(isonicotinoyl)-5-oxohexanoate which is then reacted with 35% aqueous sodium hydroixde solution at 25°–30° C. to produce ethyl 3-(4-pyridinyl)-2-cyclohexen-1-one-4-carboxylate and the 4-carboxylate is heated with aqueous sulfuric acid at 95° C. until the evolution of carbon dioxide ceases, thereby producing 3-(4-pyridinyl)-2-cyclohexen-1-one.

C. 3-(3- OR 4-PYRIDINYL)-2-CYCLOHEXEN-1-ONE OXIMES

C-1. 3-(4-Pyridinyl)-2-cyclohexen-1-one oxime — In a 5liter 3 necked flask 280 g. of hydroxylamine hydrochloride was dissolved in 2200 ml. of pyridine and with stirring 327 g. of 3-(4-pyridinyl)-2-cyclohexen-1-one was added portionwise. The reaction mixture was heated on a steam bath for two and one-half hours and the pyridine was distilled off under reduced pressure. To the residue was added cold water; the mixture was stirred well; and, it was then basified with ammonium hydroxide. The solid was collected, washed well with water and dried in vacuo at 70° C. to yield 335 g. of 3-(4-pyridinyl)-2-cyclohexen-1-one oxime, m.p. 178°-181° C. (93% yield).

C-2. 3-(3-Pyridinyl)-2-cyclohexen-1-one oxime — A mixture containing 55.5 g. of 3-(3-pyridinyl)-2-cyclohexen-1-one, 35.0 g. of hydroxylamine hydrochloride and 150 ml. of pyridine was heated on a steam bath for three hours and then poured in 1500 ml. of water. The resultinhg white solid was collected, washed with water and recrystallized from acetonitrile containing about 10% methanol to yield 46.1 g. of 3-(3-pyridinyl)-2-cyclohexen-1-one oxime, m.p. 163°-165° C.

C-3. 3-(2-Methyl-5-pyridinyl)-2-cyclohexen-1-one oxime, 6.0 g., m.p. 167°-171° C., was prepared as in Example C-2 using 13.1 g. of 3-(2-methyl-5-pyridinyl)-2-cyclohexen-1-one, 9.5 g. of hydroxylamine hydrochloride, 40 ml. of pyridine, refluxing for four hours and crystallization from acetonitrile.

Following the procedure described in Example C-1 but using in place of 3-(4-pyridinyl)-2-cyclohexen-1-one a molar equivalent quantity of the appropriate 3-(pyridinyl)-2-cyclohexen-1-one, the 3-(pyridinyl)-2-cyclohexen-1-one oximes of Examples C-4 thru C-15 are obtained.

C-4. 3-(2-Methyl-4-pyridinyl)-2-cyclohexen-1-one oxime using 3-(3-methyl-4-pyridinyl)-2-cyclohexen-1-one.

C-5. 3-(5-Ethyl-3-pyridinyl)-2-cyclohexen-1-one oxime using 3-(5-ethyl-3-pyridinyl)-2-cyclohexen-1-one.

C-6. 3-(4-Methyl-3-pyridinyl)-2-cyclohexen-1-one oxime using 3-(4-methyl-3-pyridinyl)-2-cyclohexen-1-one.

C-7. 3-(2,4-Dimethyl-3-pyridinyl)-2-cyclohexen-1-one oxime using 3-(2,4-dimethyl-3-pyridinyl)-2-cyclohexen-1-one.

C-8. 3-(2,6-Dimethyl-3-pyridinyl)-2-cyclohexen-1-one oxime using 3-(2,6-dimethyl-3-pyridinyl)-2-cyclohexen-1-one.

C-9. 3-(2,6-Dimethyl-4-pyridinyl)-2-cyclohexen-1-one oxime using 3-(2,6-dimethyl-4-pyridinyl)-2-cyclohexen-1-one.

C-10. 3-(3-Methyl-4-pyridinyl)-2-cyclohexen-1-one oxime using 3-(3-methyl-4-pyridinyl)-2-cyclohexen-1-one.

C-11. 3-(2-Ethyl-4-pyridinyl)-2-cyclohexen-1-one oxime using 3-(2-ethyl-4-pyridinyl)-2-cyclohexen-1-one.

C-12. 3-(2-Methyl-3-pyridinyl)-2-cyclohexen-1-one oxime using 3-(2-methyl-3-pyridinyl)-2-cyclohexen-1-one.

C-13. 3-(5-Ethyl-2-methyl-4-pyridinyl)-2-cyclohexen-1-one oxime using 3-(5-ethyl-2-methyl-4-pyridinyl)-2-cyclohexen-1-one.

C-14. 3-(2-Ethyl-5-methyl-3-pyridinyl)-2-cyclohexen-1-one oxime using 3-(2-ethyl-5-methyl-3-pyridinyl)-2-cyclohexen-1-one.

C-15. 3-(4-Ethyl-5-methyl-3-pyridinyl)-2-cyclohexen-1-one oxime using 3-(4-ethyl-5-methyl-3-pyridinyl)-2-cyclohexen-1-one.

D. 3- OR 4-(3-AMINOPHENYL)PYRIDINES FROM 3- (3- OR 4-PYRIDINYL)-2-CYCLOHEXEN-1-ONE OXIMES

D-1. 4-(3-Aminophenyl)pyridine — To a stirred solution containing 1100 ml. of acetic acid and 170 ml. of acetic anhydride was added 168 g. of 3-(4-pyridinyl)-2-cyclohexen-1-one oxime and hydrogen chloride gas was passed through the solution until it started to reflux and was kept flowing through the reaction mixture while refluxing for six hours, external heating being provided. A precipitate started to separate after about 2 hours. The solvent was removed at reduced pressure and the solid residue was treated with about 500 ml. of water followed by 35% aqueous sodium hydroxide solution until the mixture was definitely basic. Then enough ethanol was added to make the mixture homogenous and finally it was refluxed with stirring overnight. The mixture was cooled in an ice bath and the solid was collected. The solid was washed on the filter with 50% cold ethanol and dried in a vacuum oven at 70° C. to yield 112 g. of 4-(3-aminophenyl)pyridine, m.p. 167°-171° C. A second crop of 4 g. of the product also was obtained, thereby bringing the yield to 116 g. (77%).

D-2. 3-(3-Aminophenyl)pyridine — To a mixture containing 28.9 g. of 3-(3-pyridinyl)-2-cyclohexen-1-one oxime, 42 ml. of acetic acid and 42 ml. of acetic anhydride was passed gaseous hydrogen chloride whereupon the temperature rose to about 120° C. The hydrogen chloride was passed continuously into the reaction mixture until the temperature fell to about 50° C. The reaction mixture was allowed to stand for three hours and then concentrated in vacuo to yield, as a glassy material, 3-(3-acetamidophenyl)pyridine. To this material was added 100 ml. of water and 25 ml. of concentrated hydrochloric acid and the resulting mixture was refluxed for sixteen hours and concentrated in vacuo to yield a yellow solid. The solid was taken up in water and the solution was made alkaline with 35% aqueous sodium hydroxide solution. The alkaline solution was extracted three times with ethylene dichloride. The extract was washeed with water, dried over anhydrous magnesium sulfate and concentrated in vacuo to yield an oil. The oil was distilled under reduced pressure, collecting the fraction boiling at 141°-145° C. at 0.15 mm. to yield, a first as a yellow oil which crystallized on cooling, 17.7 g. of 3-(3-aminophenyl)pyridine, m.p. 72°-74° C.

D-3. 5-(3-Aminophenyl)-2-methylpyridine, 8.6g., m.p. 113°-116° C., was prepared as in Example D-2 using 11.6 g. of 3-(2-methyl-5-pyridinyl)-2-cyclohexen-1-one oxime, 16 ml. of acetic acid, 16 ml. of acetic anhydride hydrogen chloride gas (passed in while the temperature rose to 110° C. for one hour), refluxing the resulting 5-(3-acetamidophenyl)-2-methylpyridine for twenty hours with 40 ml. of water and 12 ml. of hydrochloric acid, and recrystallization from isopropyl acetate.

Following the procedure described in Example D-1 but using in place of 3-(4-pyridinyl)-2-cyclohexen-1-one oxime a molar equivalent quantity of the appropriate 3-(pyridinyl)-2-cyclohexen-1-one oxime, the (3-aminophenyl)-pyridines of Examples D-4 thru D-15 are obtained.

D-4. 4-(3-Aminophenyl)-2-methylpyridine using 3-(2-methyl-4-pyridinyl)-2-cyclohexen-1-one oxime.

D-5. 3-(3-Aminophenyl)-5ethylpyridine using 3-(5-ethyl-3-pyridinyl)-2-cyclohexen-1-one oxime.

D-6. 3-(3-Aminophenyl)-4-methylpyridine using 3-(4-methyl-3-pyridinyl)-2-cyclohexen-1-one oxime.

D-7. 3-(3-Aminophenyl)-2,4-dimethylpyridine using 3(2,4-dimethyl-3-pyridinyl)-2-cyclohexen-1-one oxime.

D-8. 3(3-Aminophenyl)-2,6-dimethylpyridine using 3-(2,6-dimethyl-3-pyridinyl)-2-cyclohexen-1-one oxime.

D-9. 4-(3-Aminophenyl)-2,6-dimethylpyridine using 3-(2,6-dimethyl-4-pyridinyl)-2-cyclohexen-1-one oxime.

D-10. 4-(3-Aminophenyl)-3-methylpyridine using 3-(3-methyl-4-pyridinyl)-2-cyclohexen-1-one oxime.

D-11. 4-(3Aminophenyl)-2-ethylpyridine using 3-(2-ethyl-4-pyridinyl)-2-cyclohexen-1-one oxime.

D-12. 3-(3-Aminophenyl)-2-methylpyridine using 3-(2-methyl-3-pyridinyl)-2-cyclohexen-1-one oxime.

D-13. 4-(3-Aminophenyl)-5-ethyl-2-methylpyridine using 3-(5-ethyl-2-methyl-4-pyridinyl)-2-cyclohexen-1-one oxime.

D-14. 3-(3-Aminophenyl)-2-ethyl-5-methylpyridine using 3-(ethyl-5-methyl-3-pyridinyl)-2-cyclohexen-1-one oxime.

D-15. 3-(3-Aminophenyl)-4-ethyl-5-methylpyridine using 3-(4-ethyl-5-methyl-3-pyridinyl)-2-cyclohexen-1-one oxime.

Following the procedures described in Examples 1B, 1C, 1D and 1A of U.S. Pat. No. 3,753,993 and using in place of 4-(3-aminophenyl)pyridine [same as 3-(4-pyridinyl)aniline] the 4- or 3-(3-aminophenyl)pyridines [same as 3-PY-anilines] of Examples D-4 through D-15 herein there are obtained in the step corresponding to Example 1A of 3,753,993 the corresponding respective 1-ethyl-1,4-dihydro-4-oxo-7-PY-3-quinolinecarboxylic acid, e.g., 1-ethyl-1,4-dihydro-7-(3-methyl-4-pyridinyl)-4-oxo-3-quinolinecarboxylic acid using 4-(3-aminophenyl)-3-methylpyridine of Example D-10.

We claim:

1. The process for preparaing a 3-(pyridinyl)-2-cyclohexen-1-one having the formula

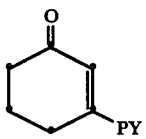

where PY is 4- or 3-pyridinyl or 4- or 3-pyridinyl having one or two lower-alkyl substituents, which comprises reacting methyl vinyl ketone with lower-alkyl 3-(pyridinyl)-3-oxo-propanoate of the formula

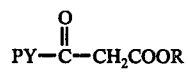

where PY is 4- or 3-pyridinyl or 4- or 3-pyridinyl having one or two lower-alkyl substituents and R is lower-alkyl, in the presence of a basic condensing agent to produce lower-alkyl 5-oxo-2-(pyridinylcarbonyl)hexanoate of the formula

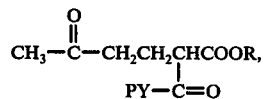

heating said hexanoate under aqueous acidic conditions thereby hydrolyzing and decarboxylating it to produce 1-PY-hexan-1,5-dione and reacting said hexan-1,5-dione with a basic condensing agent to produce said 3-PY-2-cylohexen-1-one or first reacting said lower-alkyl 5-oxo-2-(pyridinylcarbonyl)hexanoate with a basic condensing agent to produce lower-alkyl 3-(pyridinyl)-2-cyclohexen-1-one-4-carboxylate and then heating under aqueous acidic conditions to hydrolyze and decarboxylate said 4-carboxylate to produce said 3-(pyridinyl)-2-cyclohexen-1-one.

2. The process according to claim 1 where the basic condensing agent is an alkali metal lower-alkoxide in the first step and an aqueous alkali hydroxide solution in the last step.

3. The process according to claim 2 where PY is 4-pyridinyl, 3-pyridinyl, 2-methyl-4-pyridinyl or 2-methyl-5-pyridinyl.

* * * * *

UNITED STATES PATENT AND TRADEMARK OFFICE
CERTIFICATE OF CORRECTION

PATENT NO. : 4,111,946

DATED : September 5, 1978

INVENTOR(S) : Karl O. Gelotte, Andrew W. Zalay and Malcolm R. Bell

It is certified that error appears in the above-identified patent and that said Letters Patent are hereby corrected as shown below:

Column 3, line 11, "870,753 pending, filed" should read -- 870,753, filed --.

Column 5, line 31, "(n-propanoyl) butyryl" should read -- (n-propanoyl), butyryl --.

Column 6, line 15, "product" should read -- produce --.

Column 8, line 47, delete "and".

Column 11, line 58, "1.490" should read -- 1.4940 --.

Column 15, line 8, "resultinhg" should read -- resulting --.

Column 16, line 34, "washeed" should read -- washed --.

UNITED STATES PATENT AND TRADEMARK OFFICE
CERTIFICATE OF CORRECTION

PATENT NO. : 4,111,946
DATED : September 5, 1978
INVENTOR(S) : Karl O. Gelotte, Andrew W. Zalay and
Malcolm R. Bell It is certified that error appears in the above-identified patent and that said Letters Patent are hereby corrected as shown below:

Column 16, line 38, "to yield, a first as a" should read -- to yield, first as a --.

Column 17, line 11, "3-(ethyl-5-methyl-3-" should read -- 3-(2-ethyl-5-methyl-3- --.

Column 17, line 28, "preparaing" should read -- preparing --.

Signed and Sealed this

Nineteenth Day of August 1980

[SEAL]

Attest:

SIDNEY A. DIAMOND

Attesting Officer

Commissioner of Patents and Trademarks